(12) United States Patent
Toda (10) Patent No.: US 11,383,271 B2
(45) Date of Patent: Jul. 12, 2022

(54) ULTRASOUND TRANSDUCER

(71) Applicant: OLYMPUS CORPORATION, Tokyo (JP)

(72) Inventor: Masaya Toda, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 1059 days.

(21) Appl. No.: 16/012,042

(22) Filed: Jun. 19, 2018

(65) Prior Publication Data

US 2018/0297079 A1   Oct. 18, 2018

Related U.S. Application Data (63) Continuation of application No. PCT/JP2015/086122, filed on Dec. 24, 2015.

(51) Int. Cl.

| B06B 1/06 | (2006.01) |
|---|---|
| A61B 18/00 | (2006.01) |
| A61B 17/32 | (2006.01) |
| A61B 17/00 | (2006.01) |

(52) U.S. Cl.
CPC ........ *B06B 1/06* (2013.01); *A61B 17/320068* (2013.01); *A61B 18/00* (2013.01); *B06B 1/0611* (2013.01); *A61B 2017/00017* (2013.01); *A61B 2017/00106* (2013.01); *A61B 2017/320088* (2013.01); *A61B 2017/320089* (2017.08); *A61B 2018/00571* (2013.01)

(58) Field of Classification Search
CPC  A61B 17/320068; A61B 2017/320088; A61B 2017/320089; A61B 2017/00017; A61B 2017/00106; A61B 2018/00571; A61B 18/00; B06B 1/06; B06B 1/0611
See application file for complete search history.

(56) References Cited

U.S. PATENT DOCUMENTS

| 5,126,618 A | 6/1992 | Takahashi et al. |
|---|---|---|
| 8,334,635 B2 | 12/2012 | Voegele et al. |
| 2008/0184802 A1 | 8/2008 | Sato |
| 2009/0036912 A1 | 2/2009 | Wiener et al. |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |

(Continued)

FOREIGN PATENT DOCUMENTS

| CN | 101241183 A | 8/2008 |
|---|---|---|
| EP | 2514375 A2 | 10/2012 |

(Continued)

OTHER PUBLICATIONS

International Search Report dated Mar. 15, 2016 issued in PCT/JP2015/086122.

(Continued)

*Primary Examiner* — Ashley L Fishback
(74) *Attorney, Agent, or Firm* — Scully, Scott, Murphy & Presser, P.C.

(57) ABSTRACT

An ultrasound transducer includes a plurality of piezoelectric elements that are layered in the thickness direction and that generate a longitudinal vibration in the thickness direction. The plurality of piezoelectric elements are arranged so that the thicknesses thereof are sequentially larger from the antinode side of the longitudinal vibration towards the node side of the longitudinal vibration.

11 Claims, 4 Drawing Sheets

(56) References Cited

U.S. PATENT DOCUMENTS

| | | |
|---|---|---|
| 2012/0289984 A1 | 11/2012 | Houser et al. |
| 2013/0178882 A1 | 7/2013 | Voegele et al. |
| 2013/0226208 A1 | 8/2013 | Wiener et al. |
| 2014/0243864 A1 | 8/2014 | Voegele et al. |
| 2016/0374708 A1 | 12/2016 | Wiener et al. |
| 2017/0007855 A1 | 1/2017 | Toda |
| 2017/0056058 A1 | 3/2017 | Voegele et al. |

FOREIGN PATENT DOCUMENTS

| | | |
|---|---|---|
| EP | 2514376 A2 | 10/2012 |
| EP | 2514377 A2 | 10/2012 |
| EP | 3127496 A1 | 2/2017 |
| EP | 3170467 A1 | 5/2017 |
| GB | 2245097 A | 12/1991 |
| JP | H03-254952 A | 11/1991 |
| JP | 2010-535089 A | 11/2010 |
| JP | 2014-226318 A | 12/2014 |
| JP | 5666576 B2 | 2/2015 |
| JP | 2016-022136 A | 2/2016 |
| WO | WO 2009/018406 A2 | 2/2009 |
| WO | WO 2011/005467 A2 | 1/2011 |

OTHER PUBLICATIONS

Chinese Office Action dated Aug. 28, 2020 in Chinese Patent Application No. 201580085414.1.

| YOUNG'S MODULUS (PIEZOELECTRIC ELEMENT/ METAL BODY) | FIRST PIEZOELECTRIC ELEMENT | SECOND PIEZOELECTRIC ELEMENT | THIRD PIEZOELECTRIC ELEMENT | FOURTH PIEZOELECTRIC ELEMENT |
|---|---|---|---|---|
| | 0.6~0.9 | 0.6~0.9 | 0.8~1.0 | 0.9~1.1 | ered # ULTRASOUND TRANSDUCER

CROSS-REFERENCE TO RELATED APPLICATIONS

This is a continuation of International Application PCT/JP2015/086122, with an international filing date of Dec. 24, 2015, which is hereby incorporated by reference herein in its entirety.

TECHNICAL FIELD

The present invention relates to an ultrasound transducer.

BACKGROUND ART

In surgical treatment, surgical instruments for performing treatment using vibrations generated by ultrasound transducers have been used (for example, refer to Patent Literature 1). The ultrasound transducer mounted in such a surgical instrument is provided with a laminated body composed of a plurality of piezoelectric elements layered in the thickness direction and is designed so that a node of a longitudinal vibration is located in the laminated body.

CITATION LIST

Patent Literature

{PTL 1}
Japanese Translation of PCT International Application, Publication No. 2010-535089

SUMMARY OF INVENTION

An aspect of the present invention is directed to an ultrasound transducer including a plurality of piezoelectric elements that are layered in a thickness direction and that generate longitudinal vibration in the thickness direction, wherein the plurality of piezoelectric elements are arranged so that the thicknesses thereof are sequentially larger from an antinode side of the longitudinal vibration towards a node side of the longitudinal vibration.

BRIEF DESCRIPTION OF DRAWINGS

FIG. 2 is (a) a side view showing the overall configuration of an ultrasound transducer in the ultrasound treatment device in FIG. 1, and (b) a rear view as seen in a direction of the longitudinal axis from a basal end side.

DESCRIPTION OF EMBODIMENTS

An ultrasound transducer 1 according to one embodiment of the present invention will now be described with reference to the drawings.

Figure 1:
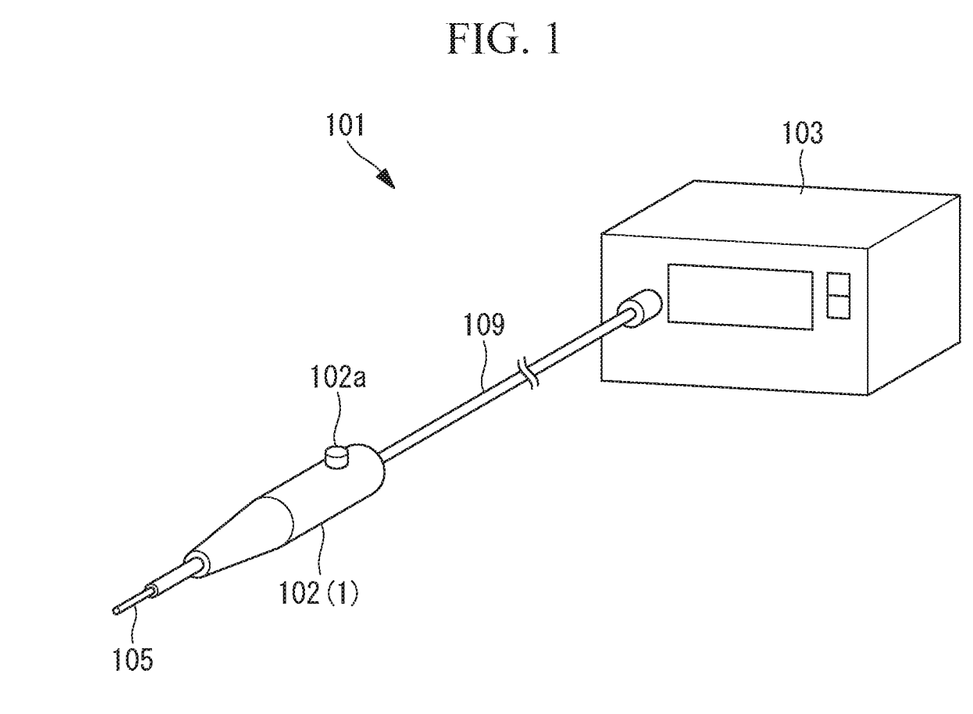
FIG. 1 is an outside view showing the overall configuration of an ultrasound treatment device according to one embodiment of the present invention.

FIG. 1 is an outside view of the overall configuration of an ultrasound treatment device 101 according to one embodiment of the present invention. As shown in FIG. 1, the ultrasound transducer 1 according to the embodiment is applied to the ultrasound treatment device 101.

As shown in FIG. 1, the ultrasound treatment device 101 includes: an ultrasound treatment tool 102 having the ultrasound transducer 1 therein; and a control unit 103 that is connected to the treatment tool 102 via a cable 109. The control unit 103 supplies a high-frequency drive voltage to the ultrasound transducer 1 and controls the drive voltage. Reference sign 105 denotes a probe, the basal end of which is fixed to the ultrasound transducer 1.

The treatment tool 102 is provided with a hand switch 102a for instructing starting and stopping of the supply of the drive voltage from the control unit 103 to the ultrasound transducer 1. When a user operates the hand switch 102a to turn it ON, a drive voltage is supplied from the control unit 103 via the cable 109. Thereby, the ultrasound transducer 1 generates ultrasound vibrations, and these ultrasound vibrations propagate through the probe 105 and vibrate a distal end portion of the probe 105. This causes frictional heat to be generated in tissue in contact with the distal end portion of the probe 105, thereby coagulating or incising the tissue. Note that the treatment tool 102 may employ a method for bringing a horn provided at a distal end of the ultrasound transducer 1 into direct contact with tissue.

Figure 2:
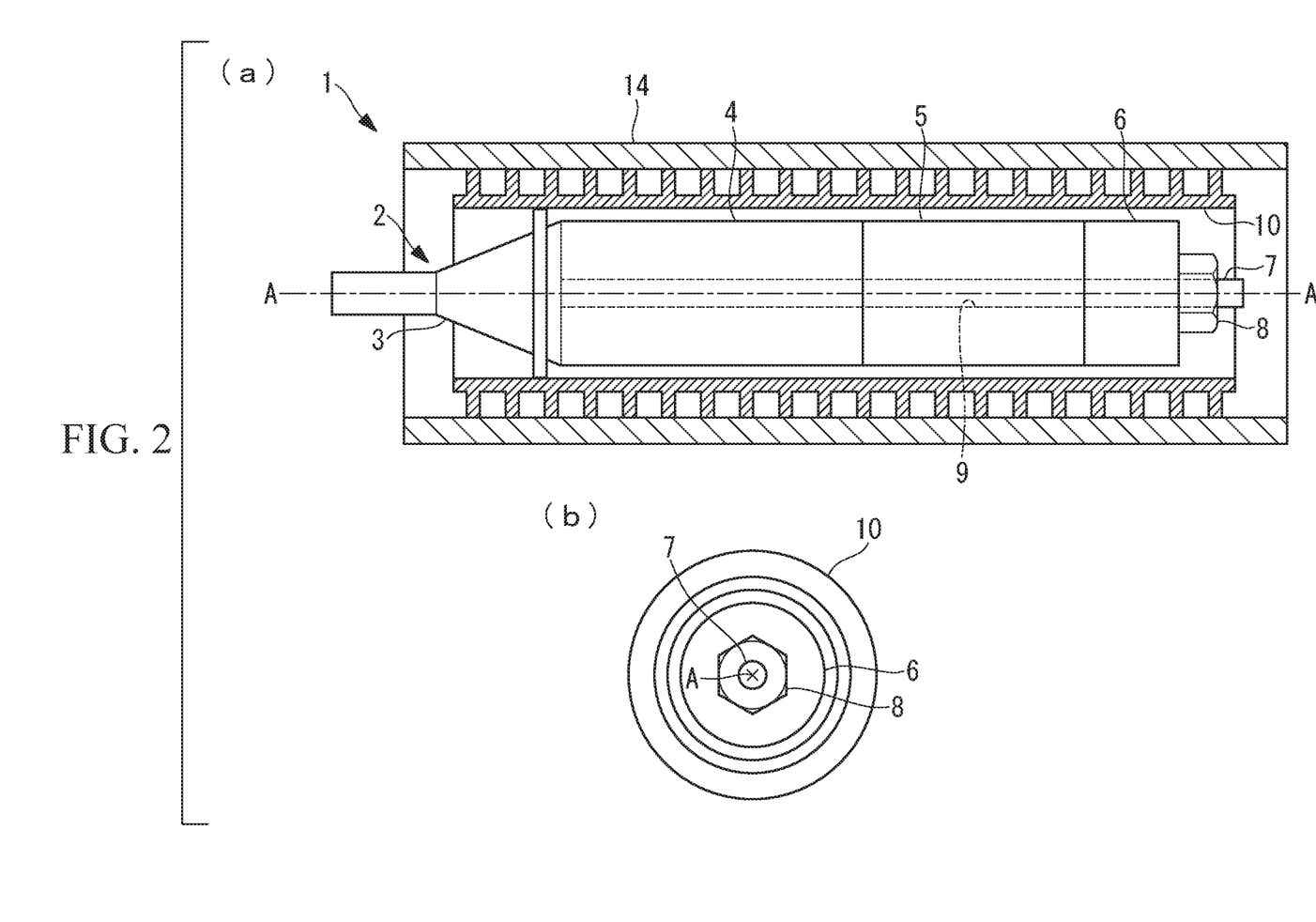

As shown in FIGS. 2(a) and (b), the ultrasound transducer 1 according to this embodiment includes: a transducer main body (hereinafter, referred to simply as the "main body") 2 composed of a bolt-clamped Langevin (BLT) transducer; and a heat-dissipation tube 10 for housing the main body 2. Reference sign 14 denotes an electrically insulating outer cylinder for covering the exterior of the ultrasound transducer 1.

The main body 2 includes a horn 3, a first metal body 4, a laminated body 5 composed of a plurality of piezoelectric elements, and a second metal body 6, in that order from the distal end side along a longitudinal axis A. In addition, the main body 2 includes a bolt 7 and a nut 8 for integrally fastening the first metal body 4, the laminated body 5, and the second metal body 6.

The horn 3 and the bolt 7 constitute a single member formed of a metal having a high ultrasound propagation efficiency and high strength and are preferably formed of 64 titanium alloy (B348 Grade 5 in the ASTM standards). The horn 3 is approximately cone-shaped and is tapered towards the distal end. The bolt 7 extends in a straight line along the longitudinal axis A from a basal end surface of the horn 3 towards the basal end side.

The first metal body 4, the laminated body 5, and the second metal body 6 have a bolt hole 9 that passes therethrough along the longitudinal axis A and into which the bolt 7 is inserted. The nut 8 is fastened at the basal end portion of the bolt 7 projecting from the basal end surface of the second metal body 6, whereby the laminated body 5 is firmly tightened from both sides by the first metal body 4 and the second metal body 6. Note that the nut 8 may be omitted by forming a female thread on the second metal body 6 to be threaded with the bolt 7 and thereby also to function as the nut 8.

When a high-frequency drive voltage from a high-frequency power supply, not shown in the figure, mounted in the control unit 103 is applied to the laminated body 5, the laminated body 5 generates a longitudinal vibration in the direction of the longitudinal axis A. The generated longitudinal vibration is transmitted to the horn 3 via the bolt 7, thereby causing the distal end of the horn 3 to vibrate in the direction of the longitudinal axis A. At this time, as a result of the longitudinal vibration being amplified while being transmitted from the basal end to the distal end of the horn 3, a vibration with a large amplitude is achieved at the distal end of the horn 3. Here, the frequency of the drive voltage is selected from within a range of 20 to 100 kHz inclusive so that the distal end, the intermediate position, and the basal end of the main body 2 form antinodes of the longitudinal vibration.

The first metal body 4 is a columnar member and is formed of a metal material having high strength and elasticity, such as a titanium alloy and an aluminum alloy.

The second metal body 6 is a columnar member and is formed of a metal material, such as a titanium alloy and an aluminum alloy.

The metal bodies 4 and 6 may be formed of ceramic having aluminum as the main constituent (e.g., duralumin).

Figure 3:
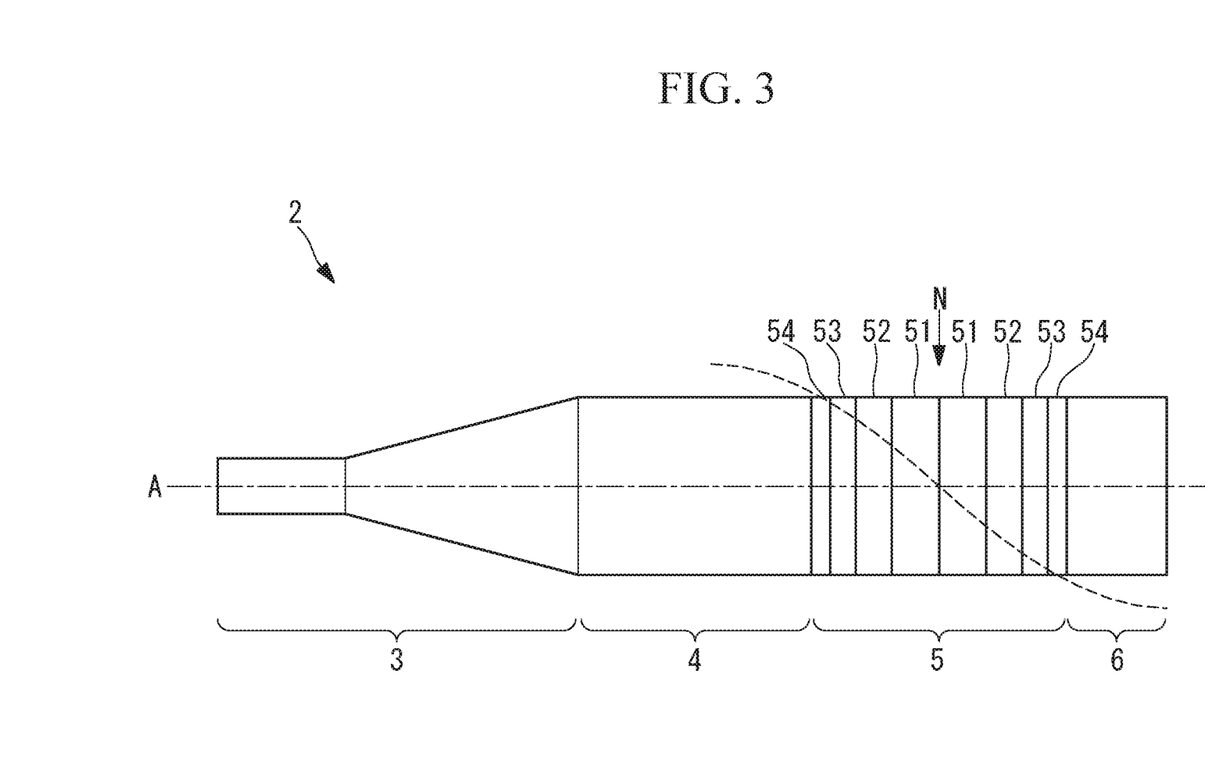
FIG. 3 is an overall configuration diagram of a main body of the ultrasound transducer in FIG. 2.

As shown in FIG. 3, the laminated body 5 includes a plurality of plate-shaped piezoelectric elements 51, 52, 53, and 54 arranged in the direction of the longitudinal axis A. The piezoelectric elements 51, 52, 53, and 54 are formed of a piezoelectric material, such as a lead zirconate titanate, a barium titanate, or a potassium sodium niobate, and are polarized in the thickness direction. The plurality of piezoelectric elements 51, 52, 53, and 54 may be formed of the same type of piezoelectric material or may be formed of different types of piezoelectric materials. Alternatively, the plurality of piezoelectric elements 51, 52, 53, and 54 may be formed of piezoelectric materials of the same type but having different physical property values.

The laminated body 5 has a layered structure in which the piezoelectric elements 51, 52, 53, and 54 and thin-plate-shaped electrodes (not shown in the figure) are alternately layered in the thickness direction such that each of the piezoelectric elements 51, 52, 53, and 54 is sandwiched between two electrodes in the thickness direction. In addition, in the laminated body 5, the polarization directions of the piezoelectric elements 51, 52, 53, and 54 are alternately reversed. An insulator, not shown in the figure, is interposed between the laminated body 5 and the first metal body 4, as well as between the laminated body 5 and the second metal body 6, whereby the laminated body 5 is electrically insulated from the first metal body 4 and the second metal body 6.

The electrodes constitute positive electrodes and negative electrodes alternately in the direction of the longitudinal axis A. All electrodes are connected in parallel via the electrical cable 109 to the common high-frequency power supply (not shown in the figure) in the control unit 103, and a common alternating voltage is applied as a drive voltage from the high-frequency power supply. As a result of the alternating voltage being applied to the electrodes, each of the piezoelectric elements 51, 52, 53, and 54 vibrates by expanding and contracting in the direction of the longitudinal axis A, thereby generating a longitudinal vibration in the entire laminated body 5 in a direction along the longitudinal axis A. The ultrasound transducer 1 is designed so that at this time, a node N of the longitudinal vibration appears in the center in the direction of the longitudinal axis A of the laminated body 5, and antinodes appear on the distal end side and the basal end side of the laminated body 5.

In the laminated body 5, the plurality of piezoelectric elements 51, 52, 53, and 54 are arranged so that the thicknesses thereof are sequentially larger from the distal end side towards the node N and the thicknesses thereof are sequentially larger from the basal end side towards the node N. In addition, the piezoelectric elements 51, 52, 53, and 54 arranged on the distal end side of the node N have different thicknesses from one another, and the piezoelectric elements 51, 52, 53, and 54 arranged on the basal end side of the node N have different thicknesses from one another. Furthermore, the distribution of the thicknesses of the piezoelectric elements 51, 52, 53, and 54 is symmetrical with respect to the node N, so that the node N is located between the two thickest piezoelectric elements 51 disposed in the center.

In the example shown in FIG. 3, a total of eight piezoelectric elements 51, 52, 53, and 54 are provided in the laminated body 5. Hereinafter, the thickest piezoelectric elements are referred to as the first piezoelectric elements 51, the second-thickest piezoelectric elements are referred to as the second piezoelectric elements 52, the third-thickest piezoelectric elements are referred to as the third piezoelectric elements 53, and the thinnest piezoelectric elements are referred to as the fourth piezoelectric elements 54. Here, as illustrated, the plurality of piezoelectric elements 51, 52, 53, and 54 are preferably arranged so that the thicknesses thereof increase sequentially from the piezoelectric elements located closest to the antinode sides towards the piezoelectric elements located closest to the node side.

Next, the operation of the ultrasound transducer 1 with this structure will be described.

In order to generate ultrasound vibration with the ultrasound transducer 1 according to this embodiment, an alternating voltage having a resonance frequency of the ultrasound transducer 1 or a frequency in proximity to the resonance frequency is supplied from the high-frequency power supply to the electrodes of the laminated body 5 via the electrical cable 109. By doing so, each of the piezoelectric elements 51, 52, 53, and 54 vibrates by expanding and contracting in the direction of the longitudinal axis A, thereby generating longitudinal vibration in the laminated body 5. The longitudinal vibration generated in the laminated body 5 is transmitted to the probe 105 via the first metal body 4 and the horn 3, and the distal end of the probe 105 vibrates in the direction of the longitudinal axis A. Therefore, biological tissue can be treated by bringing the distal end of the vibrating probe 105 into contact with the biological tissue.

Here, in the laminated body 5 being subject to longitudinal vibration, the distribution of the amounts of displacement is small at a position near the node N, large at a position near an antinode, and zero at the position of the node N. In FIG. 3, broken lines indicate the amounts of displacement at individual positions of the laminated body 5. As shown, the magnitudes of vibration generated by the piezoelectric elements 51, 52, 53, and 54 differ depending on the position in the laminated body 5.

If the thicknesses of the piezoelectric elements 51, 52, 53, and 54 are uniform, the electrical powers delivered to the piezoelectric elements 51, 52, 53, and 54 are all equal, regardless of the different amounts of displacement. Electrical power means the product of an alternating voltage and an electrical current flowing in each of the piezoelectric elements, and the electrical current flowing in each piezoelectric element depends on the thickness of the piezoelectric element, as described below. Therefore, the electrical power can be excessive in the piezoelectric elements 51 on the node N side, causing a part of the electrical power to be converted not into vibration but into heat, whereas electrical power can be insufficient in the piezoelectric elements 54 on the antinode sides, possibly failing to achieve the required vibration rates. When the alternating voltage is increased in order to increase the vibration rates of the piezoelectric elements 54 on the antinode sides, the alternating voltage supplied to the piezoelectric elements 51 on the node N side also increases, leading to an increase in the amount of heat generation. In this manner, because the proportions of work (magnitude of generated vibration) done by the piezoelectric elements with respect to delivered electrical power differ depending on the position of the piezoelectric element, electrical power is excessive or insufficient, provided that the amounts of electrical power delivered to all the piezoelectric elements are equal.

In this embodiment, the thick first piezoelectric elements 51 are disposed on the node N side where the amount of displacement is so small that low electrical power is required, whereas the thin fourth piezoelectric elements 54 are disposed on the antinode sides where the amount of displacement is so large that high electrical power is required. Therefore, an appropriate amount of electrical power required by each of the piezoelectric elements 51, 52, 53, and 54 is delivered to those piezoelectric elements. By doing so, there is an advantage in that the output (vibration rate of the distal end of the horn 3) can be increased while suppressing heat generation, making continuous driving possible in a stable manner at a high output.

More specifically, when the magnitudes of alternating voltages applied to the piezoelectric elements 51, 52, 53, and 54 are equal, the thicker a piezoelectric element, the less the electrical power is delivered to the piezoelectric element. This is because a structure in which a piezoelectric element is sandwiched between electrodes is equivalent to a capacitor and thus each piezoelectric element has a capacitance. More specifically, the thicker a piezoelectric element, the lower the capacitance and the lower the electrical current flowing in the piezoelectric element.

Therefore, by arranging the thick piezoelectric elements 51 on the node N side, the efficiency of conversion from delivered electrical power into mechanical vibration can be enhanced and thereby heat generation at the node N can be suppressed. In particular, the amount of heat generation is largest at the node N in the ultrasound transducer 1. This is because the closer a position is to the node N, the more easily electrical power is converted into heat at that position and furthermore the higher the stress occurring at the piezoelectric elements at that position. Heat generation in the entire ultrasound transducer 1 can be effectively suppressed by suppressing heat generation at the node N.

In addition, the operation of the medical ultrasound transducer 1 is restricted so that a temperature increase during driving is equal to or less than a predetermined threshold value (e.g., 20° C.). In order to efficiently drive the ultrasound transducer 1 with such a restriction, it is important to increase the magnitude of an alternating voltage as long as a temperature increase of the ultrasound transducer 1 does not exceed the threshold value. According to this embodiment, because a temperature increase of the ultrasound transducer 1 is effectively suppressed, the ultrasound transducer 1 can be efficiently driven by increasing the alternating voltage to be applied to the laminated body 5 while keeping the temperature increase of the ultrasound transducer 1 equal to or less than the predetermined threshold value.

In addition, a high vibration rate can be achieved at the distal end of the laminated body 5 by arranging the thin piezoelectric element 54 at the distal end, which is an antinode side, of the laminated body 5. The distal end of the laminated body 5 is an output end that outputs vibration to the first metal body 4, and hence it is important to increase the vibration rate at the distal end of the laminated body 5 in order to increase the vibration rate at the distal end of the first metal body 4. Therefore, according to this embodiment, the output of the ultrasound transducer 1 can be effectively increased.

Furthermore, among the piezoelectric elements having different thicknesses, the vibration transmission efficiency could decrease due to a difference in vibration rates. It should be noted, however, that the difference in thickness and the difference in vibration rate between two neighboring piezoelectric elements are controlled to be small by making the piezoelectric elements 51, 52, 53, and 54 gradually thinner from the node N towards the distal end side and towards the basal end side, thereby preventing a decrease in the vibration transmission efficiency. By doing so, the output of the ultrasound transducer 1 can be further enhanced. In particular, the difference in vibration rate between two neighboring piezoelectric elements can be controlled to be sufficiently small by providing three or more piezoelectric elements on the distal end side of the node N and also by providing three or more piezoelectric elements on the basal end side of the node N, thereby achieving a higher output.

Figure 4:
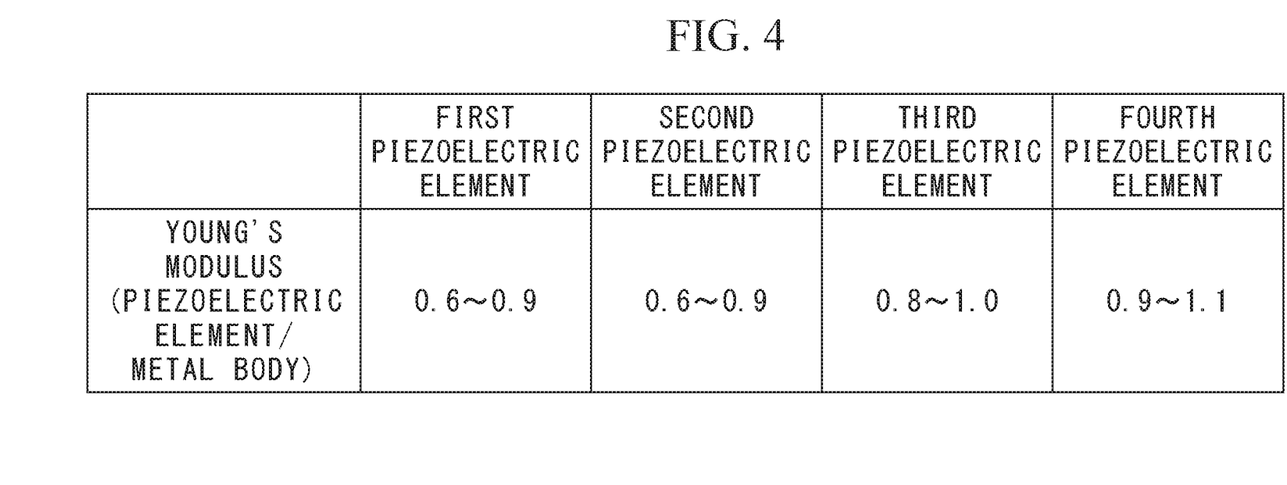
FIG. 4 is a diagram depicting one example of Young's moduli of piezoelectric elements in the ultrasound transducer in FIG. 3.

In this embodiment, as shown in FIG. 4, the piezoelectric elements 51, 52, 53, and 54 may be arranged so that the Young's moduli become sequentially lower from the distal end side towards the node N and furthermore from the basal end side towards the node N. Here, the plurality of piezoelectric elements 51, 52, 53, and 54 are preferably arranged so that the Young's moduli of the piezoelectric elements located closest to the node side are lower than the Young's moduli of the piezoelectric elements located closest to the antinode sides. In FIG. 4, the Young's modulus represents the ratio of the Young's modulus of each of the piezoelectric elements 51, 52, 53, and 54 with respect to the Young's modulus of the first metal body 4.

Because the expansion and contraction rate differs between two piezoelectric elements having different Young's moduli, the vibration transmission efficiency between the two piezoelectric elements could decrease. Therefore, it is preferable that the difference in Young's modulus between two neighboring piezoelectric elements be small. For the same reason, it is also preferable that the difference in Young's modulus between the metal body 4 or 6 and its neighboring piezoelectric element 54 be small. Because the Young's modulus of a metal material is generally higher than the Young's modulus of a piezoelectric material, a material having a high Young's modulus is used for the material of the fourth piezoelectric elements 54 neighboring the metal bodies 4 and 6. On the other hand, the first piezoelectric elements 51, to which low electrical power is delivered, are preferably formed of a material with a low Young's modulus so as to be capable of generating larger vibrations.

For the reason described above, the vibration generation efficiency and vibration transmission efficiency can be increased by arranging the plurality of piezoelectric elements 51, 52, 53, and 54 so that the Young's moduli sequentially decrease from the distal end side towards the node N and from the basal end side towards the node N, thereby making it possible to achieve an even higher output.

In this embodiment, the piezoelectric elements 51, 52, 53, and 54 may be arranged so that the piezoelectric constants increase sequentially from the distal end side towards the node N and also from the basal end side towards node N. Here, the plurality of piezoelectric elements 51, 52, 53, and 54 are preferably arranged so that the thicknesses thereof sequentially increase from the piezoelectric elements located closest to the antinode sides towards the piezoelectric elements located closest to the node side.

By doing so, there is an advantage in that an even higher output can be achieved by increasing the vibration generation efficiency from particularly the first piezoelectric elements 51.

In addition, another parameter (e.g., relative dielectric constant) associated with the vibration characteristics of the ultrasound transducer 1 may be adjusted, as appropriate, according to, for example, the piezoelectric constant and the thickness.

In this embodiment, the thicknesses of the piezoelectric elements 51, 52, 53, and 54 are all different on each of the distal end side and the basal end side of the node N. Instead of this, two or more piezoelectric elements having the same thickness may be provided on each of the distal end side and the basal end side of the node N.

In this case, two or more piezoelectric elements having the same thickness may be made to function as a set of piezoelectric elements by bonding them integrally. The plurality of sets of piezoelectric elements may be arranged side by side such that the number of bonded piezoelectric elements in each set increases sequentially from the antinode sides towards the node. In a case where the plurality of sets of piezoelectric elements are arranged in this manner, the set of the thinnest piezoelectric elements may be composed of a single piezoelectric element.

In this embodiment, the distribution of thicknesses of the piezoelectric elements 51, 52, 53, and 54 is symmetrical with respect to the node N. Instead of this, the distribution of thicknesses of the piezoelectric elements 51, 52, 53, and 54 may be asymmetrical. For example, the piezoelectric elements disposed on the distal end side of the node N and the piezoelectric elements disposed on the basal end side of the node N may have different thicknesses from each other.

With this arrangement, it is also possible to bring about a heat generation suppression effect as a result of disposing the thick piezoelectric elements on the node N side and disposing the thin piezoelectric elements on the antinode sides.

In this embodiment, the ultrasound transducer 1 generates a longitudinal vibration that has the node N in the center in the direction of the longitudinal axis A of the laminated body 5 and that has antinodes on both sides in the direction of the longitudinal axis A of the laminated body 5. However, the positions of the node and antinodes of the longitudinal vibration N are not limited to the above-described positions and can be changed as appropriate.

For example, the ultrasound transducer 1 may be designed so as to generate a longitudinal vibration that has the node N on the distal end side of the laminated body 5 and that has an antinode on the basal end side of the laminated body 5. In this case, it is advisable that a plurality of piezoelectric elements be arranged so that the thicknesses of the piezoelectric elements increase sequentially from the basal end side towards the distal end side.

As a result, the above-described embodiment leads to the following aspect.

An aspect of the present invention is directed to an ultrasound transducer including a plurality of piezoelectric elements that are layered in a thickness direction and that generate longitudinal vibration in the thickness direction, wherein the plurality of piezoelectric elements are arranged so that the thicknesses thereof are sequentially larger from an antinode side of the longitudinal vibration towards a node side of the longitudinal vibration.

According to this aspect, the piezoelectric elements can be vibrated in the thickness direction by applying a voltage to the plurality of layered piezoelectric elements in the thickness direction, thereby making it possible to generate a thickness-wise longitudinal vibration in the entire plurality of piezoelectric elements.

In this case, the plurality of piezoelectric elements are arranged so that the closer to the node a piezoelectric element is, the thicker the piezoelectric element and the closer to the antinode a piezoelectric element, the thinner the piezoelectric element. When voltages with the same magnitude are applied to the plurality of piezoelectric elements, a thicker piezoelectric element causes a lower current to flow therein, and a thinner piezoelectric element causes a higher current to flow therein. In the ultrasound transducer, a piezoelectric element on the node side is subjected to a smaller amount of displacement and hence requires a lower current, whereas a piezoelectric element on the antinode side is subjected to a larger amount of displacement and hence requires a higher current.

Therefore, it is possible to prevent an excessive electrical current from being delivered by arranging a thicker piezoelectric element on the node side, thereby suppressing heat generation at the node. In the ultrasound transducer, the amount of heat generation particularly at the node is large. Therefore, heat generation in the entire ultrasound transducer can be suppressed effectively by suppressing heat generation at the node, thereby making continuous driving possible in a stable manner at a high output. In addition, the output can be increased by arranging a thinner piezoelectric element on the antinode side. Furthermore, the vibration rates differ among the piezoelectric elements having different thicknesses. Hence, by making the piezoelectric elements sequentially thinner or thicker, a decrease in vibration transmission efficiency resulting from a difference in vibration rate between neighboring piezoelectric elements can be prevented, thereby further increasing the output.

In the above-described aspect, the plurality of piezoelectric elements may be arranged so that the thicknesses thereof are sequentially larger from a piezoelectric element located closest to the antinode side towards a piezoelectric element located closest to the node.

In the above-described aspect, the plurality of piezoelectric elements may be arranged so that the piezoelectric constants thereof are higher sequentially from the antinode side towards the node side or may be arranged so that the piezoelectric constants thereof are sequentially higher from a piezoelectric element located closest to the antinode side towards a piezoelectric element located closest to the node.

Furthermore, in the above-described aspect, the plurality of piezoelectric elements may be arranged so that the Young's moduli thereof are sequentially lower from the antinode side towards the node side or may be arranged so that the Young's modulus of a piezoelectric element located closest to the node side is lower than the Young's modulus of a piezoelectric element located closest to the antinode side.

By doing so, the vibration generation efficiency and the vibration transmission efficiency can be further enhanced while maintaining a high heat-generation suppression effect.

In the above-described aspect, the plurality of piezoelectric elements may generate the longitudinal vibration that has an antinode at a midway point in the thickness direction of the plurality of piezoelectric elements and that has antinodes on both sides in the thickness direction of the plurality of piezoelectric elements.

In the above-described aspect, the piezoelectric elements arranged on each of one side and another side of the node in the thickness direction may have different thicknesses from each other.

By doing so, the difference in thickness between two neighboring piezoelectric elements can be controlled to be smaller, thereby making it possible to further enhance the output.

In the above-described aspect, the plurality of piezoelectric elements may be arranged so that a distribution of the thicknesses is symmetrical with respect to the node.

By doing so, symmetrical heat-generation suppression effects are brought about on both sides of the node, and hence heat generation of the entire ultrasound transducer can be even more effectively suppressed.

In the above-described aspect, the number of piezoelectric elements arranged on each of one side and another side of the node in the thickness direction may be three or more.

By doing so, the difference in thickness between two neighboring piezoelectric elements can be controlled to be smaller, thereby making it possible to further enhance the output.

The present invention affords an advantage in that heat generation can be suppressed, thereby making continuous driving possible in a stable manner at a high output.

REFERENCE SIGNS LIST

1 Ultrasound transducer
4 First metal body
5 Laminated body
6 Second metal body
51, 52, 53, 54 Piezoelectric element
N Node

The invention claimed is:

1. An ultrasound transducer comprising a plurality of piezoelectric elements that are layered along a longitudinal axis and that generate a longitudinal vibration in a longitudinal axis direction,
wherein the plurality of piezoelectric elements are arranged so that the thicknesses thereof in the longitudinal axis direction are sequentially larger from an antinode side of the longitudinal vibration towards a node side of the longitudinal vibration, and are arranged so that the Young's moduli thereof are sequentially lower from the antinode side towards the node side.

2. The ultrasound transducer according to claim 1, wherein the plurality of piezoelectric elements are arranged so that the thicknesses thereof in the longitudinal axis direction are sequentially larger from a piezoelectric element located closest to the antinode side towards a piezoelectric element located closest to the node.

3. The ultrasound transducer according to claim 1, wherein the plurality of piezoelectric elements are arranged so that the piezoelectric constants thereof are sequentially higher from the antinode side towards the node side.

4. The ultrasound transducer according to claim 1, wherein the plurality of piezoelectric elements are arranged so that the piezoelectric constants thereof are sequentially higher from a piezoelectric element located closest to the antinode side towards a piezoelectric element located closest to the node.

5. The ultrasound transducer according to claim 1, wherein the plurality of piezoelectric elements are arranged so that the Young's modulus of a piezoelectric element located closest to the node side is lower than the Young's modulus of a piezoelectric element located closest to the antinode side.

6. The ultrasound transducer according to claim 1, wherein the plurality of piezoelectric elements generate the longitudinal vibration that has an antinode at a midway point in the longitudinal axis direction of the plurality of piezoelectric elements and that has antinodes on both sides in the longitudinal axis direction of the plurality of piezoelectric elements.

7. The ultrasound transducer according to 6, wherein the piezoelectric elements arranged on each of one side and another side of the node in the longitudinal axis direction have different thicknesses in the longitudinal axis direction from each other.

8. The ultrasound transducer according to claim 6, wherein the plurality of piezoelectric elements are arranged so that a distribution of the thicknesses in the longitudinal axis direction is symmetrical with respect to the node.

9. The ultrasound transducer according to claim 1, wherein the number of piezoelectric elements arranged on each of one side and another side of the node in the longitudinal axis direction is three or more.

10. An ultrasound treatment tool comprising:
an ultrasound transducer including a plurality of piezoelectric elements that are layered along a longitudinal axis and that generate a longitudinal vibration in a longitudinal axis direction; and
a probe for propagating the longitudinal vibration generated by the ultrasound transducer,
wherein the plurality of piezoelectric elements are arranged so that the thicknesses thereof in the longitudinal axis direction are sequentially larger from an antinode side of the longitudinal vibration towards a node side of the longitudinal vibration, and are arranged so that the Young's moduli thereof are sequentially lower from the antinode side towards the node side.

11. An ultrasound treatment device comprising:
an ultrasound treatment tool including an ultrasound transducer including a plurality of piezoelectric elements that are layered along a longitudinal axis and that generate a longitudinal vibration in a longitudinal axis direction, and a probe for propagating the longitudinal vibration generated by the ultrasound transducer; and
a control unit that controls a driving voltage that is supplied to the ultrasound transducer,
wherein the plurality of piezoelectric elements are arranged so that the thicknesses thereof in the longitudinal axis direction are sequentially larger from an antinode side of the longitudinal vibration towards a node side of the longitudinal vibration, and are arranged so that the Young's moduli thereof are sequentially lower from the antinode side towards the node side.

* * * * *